United States Patent
Wayne et al.

(10) Patent No.: US 9,943,347 B2
(45) Date of Patent: Apr. 17, 2018

(54) MEDIAL COLUMN (MECO) FIXATION DEVICE, METHOD, AND SYSTEM

(71) Applicant: Virginia Commonwealth University, Richmond, VA (US)

(72) Inventors: Jennifer S. Wayne, Richmond, VA (US); Robert S. Adelaar, Richmond, VA (US); Jacob E. Park, Richmond, VA (US); Brian A. Smith, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 360 days.

(21) Appl. No.: 14/803,702

(22) Filed: Jul. 20, 2015

(65) Prior Publication Data

US 2016/0022340 A1 Jan. 28, 2016

Related U.S. Application Data

(60) Provisional application No. 62/027,639, filed on Jul. 22, 2014.

(51) Int. Cl.
*A61B 17/72* (2006.01)
*A61B 17/17* (2006.01)
*A61B 17/68* (2006.01)
*A61B 17/86* (2006.01)

(52) U.S. Cl.
CPC ...... *A61B 17/7291* (2013.01); *A61B 17/1725* (2013.01); *A61B 17/68* (2013.01); *A61B 17/8625* (2013.01); *A61B 2017/8655* (2013.01)

(58) Field of Classification Search
CPC . A61B 17/72; A61B 17/7233; A61B 17/7241; A61B 17/725; A61B 17/7291; A61B 17/86; A61B 17/8625; A61B 17/863; A61B 17/8635; A61B 17/864
USPC ............................ 606/300–321, 323, 329
See application file for complete search history.

(56) References Cited

U.S. PATENT DOCUMENTS

| | | | |
|---|---|---|---|
| 6,443,954 B1 * | 9/2002 | Bramlet | A61B 17/744 606/304 |
| 6,562,042 B2 * | 5/2003 | Nelson | A61B 17/1721 606/328 |
| 7,931,651 B2 * | 4/2011 | Webb | A61B 17/60 606/304 |
| 8,920,476 B2 * | 12/2014 | Tyber | A61B 17/1717 606/279 |

(Continued)

OTHER PUBLICATIONS

IO Fix Plus Intraosseous Fixation. Surgical Technique Guide. Jun. 2012. Extremity Medical. Parsippany, NJ.

(Continued)

*Primary Examiner* — Eric S Gibson
(74) *Attorney, Agent, or Firm* — Whitham, Curtis & Cook (57) ABSTRACT

An orthopedic implant device and system support the fusion of bones in the medial column of the human foot. An exemplary implant uses an improved lag screw and supplemental components, including a washer plate and transverse screws which penetrate transverse through holes in the shaft of the lag screw. Additionally, a surgical procedure is described which may employ such an implant. The improved lag screw may be inserted at the plantar surface of the first metatarsal and support the fusion of, for example, the transverse tarsal joint, the cuneonavicular joint, and the tarsometatarsal joint.

11 Claims, 5 Drawing Sheets

(56) References Cited

U.S. PATENT DOCUMENTS

| | | | |
|---|---|---|---|
| 9,713,484 B2* | 7/2017 | Sammarco | A61B 17/7241 |
| 2003/0229346 A1* | 12/2003 | Oribe | A61B 17/70 606/246 |
| 2004/0006345 A1* | 1/2004 | Vlahos | A61B 17/8625 606/916 |
| 2004/0260288 A1* | 12/2004 | Means, Jr. | A61B 17/742 606/65 |
| 2004/0267265 A1* | 12/2004 | Kyle | A61B 17/7098 606/304 |
| 2005/0075637 A1* | 4/2005 | Semet | A61B 17/72 606/304 |
| 2006/0106389 A1* | 5/2006 | Reber | A61B 17/1721 606/309 |
| 2006/0129153 A1* | 6/2006 | Klaue | A61B 17/68 606/916 |
| 2006/0149259 A1* | 7/2006 | May | A61B 17/1714 623/13.12 |
| 2006/0173461 A1* | 8/2006 | Kay | A61B 17/8625 606/304 |
| 2006/0206044 A1* | 9/2006 | Simon | A61B 17/7216 602/23 |
| 2008/0221574 A1* | 9/2008 | Cavallazzi | A61B 17/1739 606/62 |
| 2009/0118733 A1* | 5/2009 | Orsak | A61B 17/60 606/60 |
| 2009/0265003 A1* | 10/2009 | Re | A61B 17/1714 623/13.14 |
| 2010/0121324 A1* | 5/2010 | Tyber | A61B 17/1717 606/62 |
| 2010/0152740 A1* | 6/2010 | O'Reilly | A61B 17/1615 606/87 |
| 2010/0256638 A1* | 10/2010 | Tyber | A61B 17/1717 606/62 |
| 2010/0256639 A1* | 10/2010 | Tyber | A61B 17/1717 606/62 |
| 2010/0298887 A1* | 11/2010 | Jordan | A61B 17/7098 606/304 |
| 2010/0324556 A1* | 12/2010 | Tyber | A61B 17/1717 606/62 |
| 2011/0118792 A1* | 5/2011 | Orsak | A61B 17/1615 606/301 |
| 2011/0160728 A1* | 6/2011 | Blitz | A61B 17/1725 606/64 |
| 2011/0313420 A1* | 12/2011 | LeCronier | A61B 17/7233 606/62 |
| 2012/0053639 A1* | 3/2012 | Grant | A61B 17/864 606/301 |
| 2012/0123485 A1* | 5/2012 | Dehnad | A61B 17/7266 606/304 |
| 2012/0197255 A1* | 8/2012 | Elghazaly | A61B 17/7241 606/64 |
| 2012/0239052 A1* | 9/2012 | Beger | A61B 17/8685 606/96 |
| 2013/0150903 A1* | 6/2013 | Vincent | A61B 17/1725 606/301 |
| 2013/0274818 A1* | 10/2013 | Goshayeshgar | A61B 17/8625 606/310 |
| 2013/0296862 A1* | 11/2013 | Brigido | A61B 17/1725 606/64 |
| 2013/0345763 A1* | 12/2013 | Kang | A61B 17/7098 606/329 |
| 2014/0066995 A1* | 3/2014 | McCormick | A61B 17/1728 606/281 |
| 2014/0074175 A1* | 3/2014 | Ehler | A61B 17/7055 606/329 |
| 2014/0135850 A1* | 5/2014 | Parent | A61B 17/68 606/304 |
| 2014/0188223 A1* | 7/2014 | Jensen | A61B 17/7071 623/17.11 |
| 2014/0330274 A1* | 11/2014 | Matityahu | A61B 17/744 606/64 |
| 2015/0190187 A1* | 7/2015 | Parent | A61B 17/8685 606/305 |
| 2016/0022340 A1* | 1/2016 | Wayne | A61B 17/1725 606/304 |
| 2016/0058484 A1* | 3/2016 | McCombs-Stearnes | A61B 17/7283 606/62 |
| 2016/0157902 A1* | 6/2016 | Simon | A61B 17/7216 606/64 |
| 2016/0199113 A1* | 7/2016 | Penzimer | A61B 17/0642 606/304 |
| 2016/0354127 A1* | 12/2016 | Lundquist | A61B 17/7233 |
| 2017/0007303 A1* | 1/2017 | Hansson | A61B 17/1721 |
| 2017/0056077 A1* | 3/2017 | Fallin | A61B 17/7208 |

OTHER PUBLICATIONS 6.5 mm Midfoot Fusion Bolt: For intramedullary fixation of the medial column of the foot. Technique Guide. Jun. 2009. Synthes (USA). West Chester, PA.

* cited by examiner

MEDIAL COLUMN (MECO) FIXATION DEVICE, METHOD, AND SYSTEM

CROSS-REFERENCE TO RELATED APPLICATIONS

This application claims the priority of U.S. Provisional Patent Application No. 62/027,639, filed Jul. 22, 2014, the complete contents of which are herein incorporated by reference.

FIELD OF THE INVENTION

The invention generally relates to the field of orthopedic implant devices and, more particularly, surgical solutions for midfoot arthrodesis.

BACKGROUND

Midfoot arthrodesis, which involves the fusion of bones in the medial column, is a common treatment for a number of foot deformities and conditions. Conventional lag screws are a common surgical implant device employed for midfoot athrodesis. A surgical lag screw generally comprises a head and a shaft which is partially threaded at the end which is opposite the head. A portion of the shaft immediately adjacent the head is generally smooth and without threads. For purposes of bone fusion, a lag screw generally works by engaging the threaded portion of the shaft into a bone and, in combination with the head of the screw, compressing the bone in which the threads are imbedded against a neighboring bone through which the smooth portion of the screw shaft passes. The compressive forces between the bones is referred to as the lag effect. Lag screws may be cannulated with a hollow center. This permits alignment with a guide wire or guide pin.

IO Fix (trademark of Extremity Medical) is a surgical implant generally comprising a pair of screws, with a first screw imbedded in a single bone and a second screw imbedded in two adjacent bone structures, supplying a lag effect therebetween. The first screw gives support to the second screw and changes the distribution of compression forces.

The Midfoot Fusion Bolt (by DePuy Synthes) is an intramedullary implant that can be used to fuse the medial metatarsocuneiform, naviculocuneiform, and talonavicular joints. The implant generally comprises a solid bolt which is inserted through the upper center of the first metatarsal head close to the dorsal cortex.

US Patent App. Pub. No. 2010/0256639 A1 describes an intramedullary fixation assembly having a first member and a second member. After insertion into the bone, the first and second members are held in place by pairs of retaining screws which pass through the first and second members.

In spite of existing solutions, post-operative problems still exist for some patients after a midfoot arthrodesis procedure. The main problems with diabetic Charcot medial column fusion are non-rigid fixation and wound infection with prominent hardware. Furthermore, many existing solutions are undesirable and cost prohibitive. Despite the surgery's intent to rigidly fix the bones for which fusion is desired, small and potentially deleterious movement does sometimes still occur between the bones, inhibiting or preventing the body's induced fusion by ossification. This arises from limitations of the existing surgical implants. Traditional lag screws, for example, may sometimes rotate or shift and loosen the compressive forces between the bones. In addition, many of the existing solutions do not allow for fusion of more than two bones. As a result, it is not uncommon for several implants, e.g. several conventional lag screws, to be needed for the fusion of three or more bones in the midfoot.

SUMMARY

An orthopedic implant device and system are described which support the fusion of bones in the medial column of the human foot. An exemplary implant uses an improved lag screw and supplemental components, including a washer plate and transverse screws which penetrate transverse through holes in the shaft of the lag screw. Additionally, a surgical procedure is described which may employ such an implant. The improved lag screw may be inserted at the plantar surface of the first metatarsal, a novel insertion point over existing solutions for midfoot arthrodesis. In an exemplary embodiment, an implant is provided which supports the fusion of the transverse tarsal (talonavicular) joint, the cuneonavicular joint, and the tarsometatarsal joint of the midfoot.

No other system currently on the market has an insertion point on the plantar surface of the first metatarsal, contains through-holes as described herein, or includes a washer plate on the first metatarsal. The proposed device, system, and methods simplify the process of installing compression along Meary's Line. They may be considered an improvement to the standard lag screw. Generally, exemplary embodiments provide a more rigid configuration with interlocked fusion sites and are not prominent as in a plate/screw construct which can be compromised with wound breakdown.

DETAILED DESCRIPTION

Figure 1A:
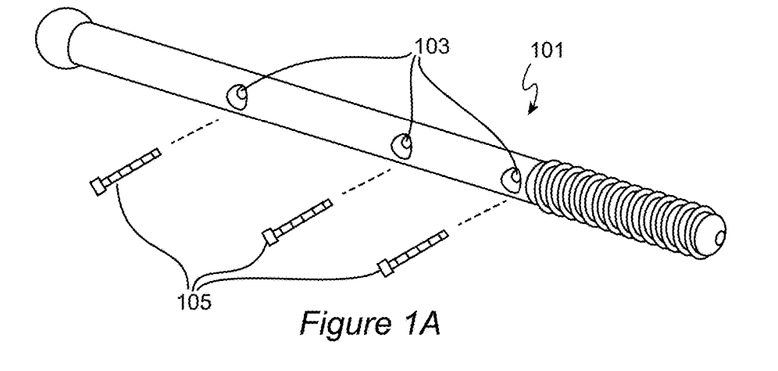
FIGS. 1A-1C show different views of an exemplary lag screw.
Figure 1B:
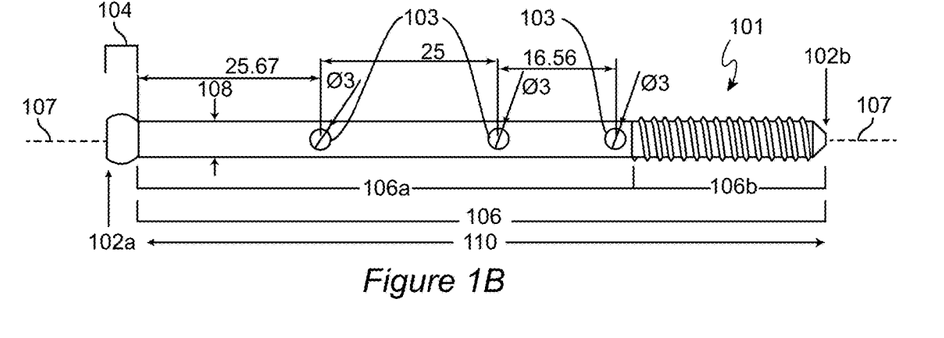
Figure 1C:
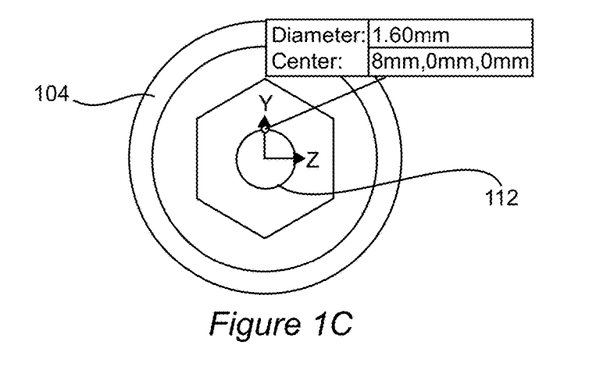

Referring now to the figures, and more particularly FIGS. 1A-1C, a lag screw 101 is provided which, after implantation, penetrates two or more bones of one or more joints and induces compressive forces therebetween which are required for fusion. In some exemplary embodiments, the lag screw 101 is of sufficient length to penetrate the bones of one or more of the transverse tarsal (talonavicular) joint, the cuneonavicular joint, and the tarsometatarsal joint. As used herein, "penetrate" describes insertion of one object into another. Penetration may be only partial, in that the penetrating element is inserted into the penetrated element without reemerging at another location. Alternatively, penetration may be such that the penetrating element passes through the penetrated element such that it enters at one location and emerges at a second location of the penetrated element. In the case of a lag screw 101 which is linear, penetration through a bone means the lag screw enters one side of the bone and exits at an opposite side of the bone. On the other hand, if a lag screw 101 simply penetrates a bone, it may pass entirely through the bone or only penetrate up to a certain depth, the inserted end remaining imbedded at some depth within the bone.

As illustrated in FIGS. 1A-1C, a lag screw 101 includes a head 104 at end 102a and a shaft 106 extending from the head 104 to end 102b. The end 102a may sometimes be referred to as the distal end of the lag screw 101, and the end 102b may sometimes be referred to as the proximal end of the lag screw 101. The use of "proximal" and "distal" may correspond to the placement of the device in a patient's body, where the proximal end is the portion closest to the body proper and the distal end is the portion further away. Generally, a shaft 106 will have an unthreaded portion 106a adjacent to the head 104 and a threaded portion 106b at or near the end 102b. The lag screw 101 may be made with a material which includes tantalum and/or other elements or chemicals which encourage in-growth. The dimensions indicated in the drawings are by way of example and are not intended to be limiting. The core diameter 108 and the length 110 of the shaft may vary, especially in order to accommodate the different sized anatomies of different patients. For example, the core diameter 108 and length 110 of a shaft for a child's implant may be smaller than those for an adult's implant. As one specific example, a lag screw 101 may have a total length of 100 mm with 25 mm of threading and may furthermore be cannulated for a 1.6 mm diameter k-wire. Transverse through holes (e.g., 3 mm in diameter) may be positioned in locations where transverse screws will be inserted into the middle of each bone. These example measurements were taken from x-ray scans. Variations of screw length and transverse through hole positions/placement may be used to create a large variety of lag screws for use in a broad range of patients. In addition, a length 110 may also vary according to the number of joints which are to be fused (e.g. a shorter length 110 may be used if fusing fewer joints). For example, in different embodiments, one joint, two joints, or three joints may be fused.

To create a higher level of fusion stability, the lag screw 101 may have one or more transverse through holes 103 in key locations which permit installation of one or more transverse screws 105. The transverse through holes 103 are spaced away from the end 102a towards the end 102b of the lag screw 101. In some exemplary embodiments, at least one transverse screw 105 is installed in each bone of the two or more bones which are to be fused. The transverse through holes 103 may be arranged at any non-zero angle with respect to a center longitudinal axis 107 of the lag screw 101 or, more particularly, of the shaft 106 thereof. In an exemplary embodiment, the transverse through holes 103 are perpendicular to the center longitudinal axis 107 of the shaft 106. This arrangement provides advantages such as easier alignment of the transverse screws 105 with the transverse through holes 103 when the transverse screws 105 are being installed in the transverse through holes 103.

The transverse screws 105 help ensure the lag screw 101 does not loosen over time by locking. In some exemplary embodiments, a lag screw 101 has a plurality of transverse through holes 103. Generally, an individual transverse screw 105 may be arranged in each of the transverse through holes 103. However, it is not required in all embodiments that each transverse through hole 103 have a transverse screw 105 installed. As an example, a lag screw 101 may have three transverse through holes 103, such as is shown in FIGS. 1A and 1B, and yet any combination of one, two, or three such transverse through holes 103 may have a transverse screw 105 installed. A transverse screw 105 is preferably solid to avoid breaking.

In some exemplary embodiments, a lag screw 101 is cannulated, as shown by the cannula passage 112 shown in FIG. 1C. This permits the use of a guide wire (e.g. a k-wire) or a guide pin for drilling and inserting the lag screw 101.

Figure 2:
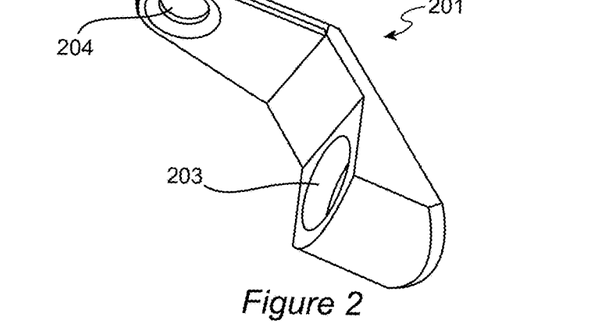
FIG. 2 shows an exemplary washer plate.

In order to achieve greater compression across the joints as well as an even level of compression on the proximal head of the first metatarsal, a washer plate 201 such as is shown in FIG. 2 may be arranged between the head 104 of the lag screw and the surface of the first metatarsal. Generally, a washer plate 201 may include an inferior hole 203 and a superior hole 204. The inferior hole 203 is sized such that the shaft 106 of the lag screw 101 may pass through but the head 104 cannot. That is to say, the diameter of the inferior hole 203 must be at least as large as the core diameter 108 of the shaft of the lag screw and should be smaller than a diameter of the head 104. A countersink, counterbore, or other depression configured to receive an underside of the head 104 may be provided with the inferior hole 203. A superior hole 204 may be included with a position displaced and at an angle with respect to the inferior hole 203, such that when the washer plate 201 is fitted to a plantar surface of the first metatarsal, the center axis of the inferior hole 203 is directed toward the adjacent bone (i.e. the medial cuneiform) while the center axis of the superior hole 204 is directed toward the diaphysis of the first metatarsal. This configuration permits installation of a screw in the diaphysis of the first metatarsal at the superior hole 204. The diameter of the superior hole 204 should be smaller than the head of the screw installed in the diaphysis to prevent the head from passing through the washer plate 204. The size of a washer plate 201 may be optimized to ensure sufficient distribution of compressive forces along the washer plate to bone interface to prevent bone from the first metatarsal breaking off from excessive loading. In an alternative exemplary embodiment, a bored out coned washer may be used instead of a washer plate 204.

Figure 3A:
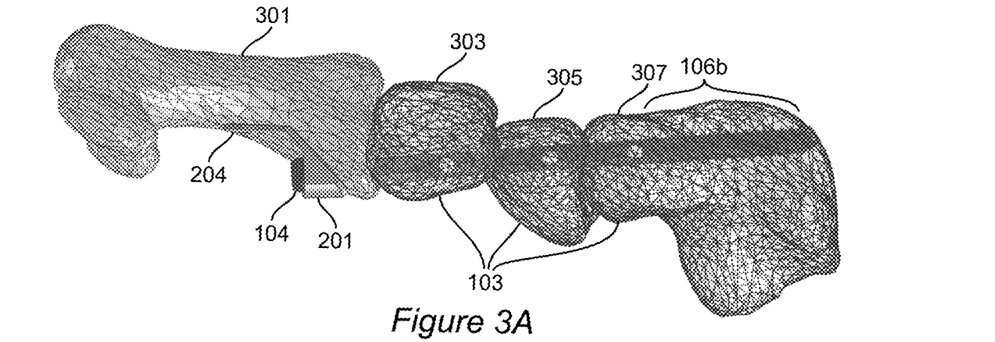
FIGS. 3A and 3B shows an exemplary orthopedic implant installed in a midfoot for arthrodesis of the transverse tarsal joint, the cuneonavicular joint, and the tarsometatarsal joint.
Figure 3B:
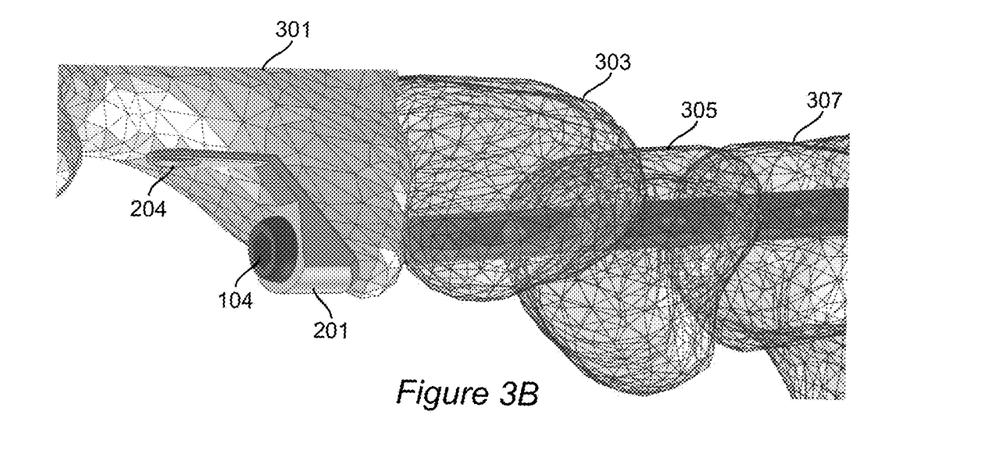

FIGS. 3A and 3B show an implant which has been arranged in a midfoot. In this exemplary example, a lag screw 101 has been inserted into a hole which penetrates each of the first metatarsal 301, the medial cuneiform 303, the navicular 305, and the talus 307. As a result, this exemplary implant gives midfoot arthrodesis of the transverse tarsal joint, the cuneonavicular joint, and the tarsometatarsal joint. A washer plate 201 is fitted on a plantar surface of the first metatarsal 301. The lag screw 101 penetrates through each of the first metatarsal 301, the medial cuneiform 303, and the navicular 305. In this example, only unthreaded portion 106a of the shaft 106 is located within the through hole drilled through these three bones 301, 303, and 305. In contrast, the entirety of the threaded portion 106b is embedded in and engaged with the talus 307. The lag screw 101 is inserted and screwed into place in such a manner that the washer plate 204 and all four bones 301, 303, 305, and 307 are pulled toward one another, creating compressive forces between abutting surfaces. The compressive forces between two bones stimulate ossification and thus fusion at the sites of compression. As shown in FIGS. 3A and 3B, transverse through holes 103 are spaced along the shaft 106 such that at least one transverse through hole 103 is positioned inside of each of the bones 303, 305, and 307. As a result, at least one transverse screw 105 may be inserted into each of these bones. Alternatively, just one or any combination of two transverse screws 105 may be inserted into any of the three transverse through holes 103 and the bone corresponding thereto. The transverse screws 105 should have a length sufficient to at least partially be present in a transverse through hole 103 and at least partially be present in one of the bones 303, 305, and 307. In some exemplary embodiments, one or more transverse screws 105 may be passed through transverse through holes 103 such that they are at least partially imbedded in bone tissue to each side of a transverse through hole 103.

Figure 4A:
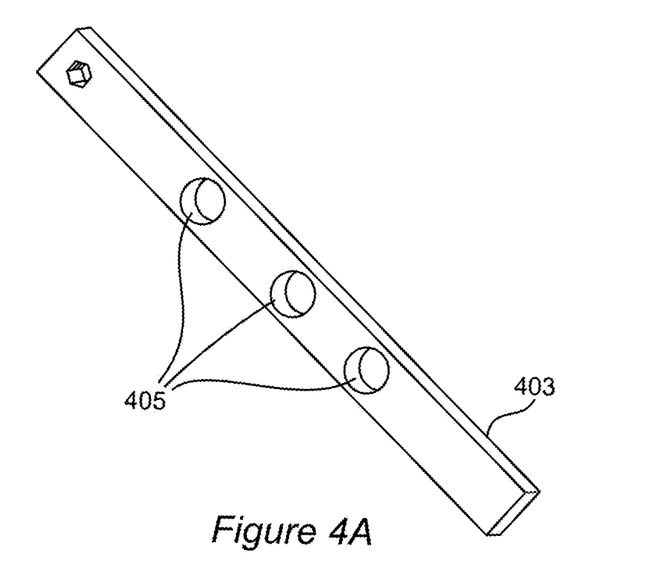
FIGS. 4A and 4B show elements of an exemplary guide for drilling and installing transverse screws in a lag screw.
Figure 4B:
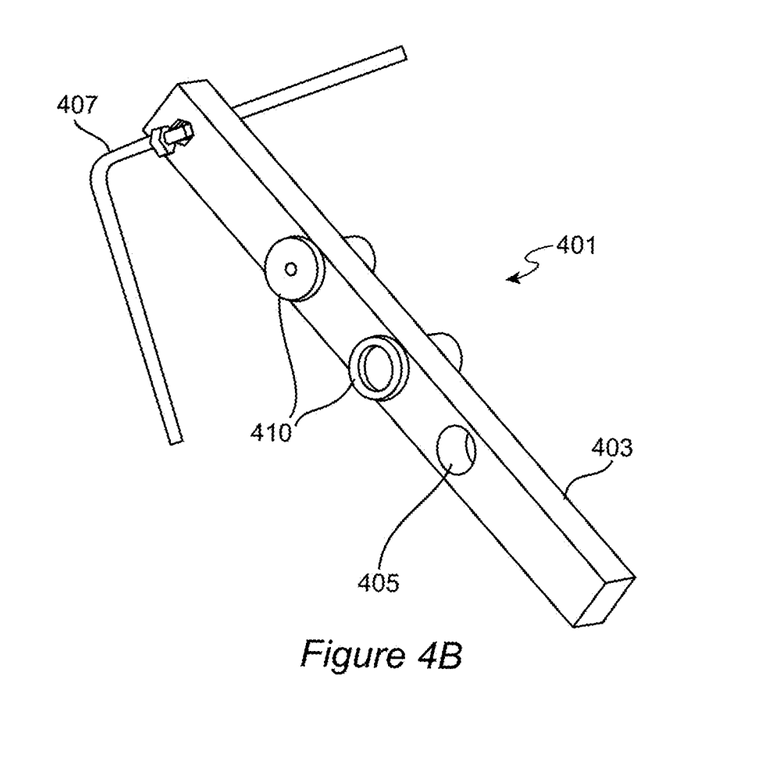

Because the lag screw 101 must be fully inserted into the two or more bones of the joints being immobilized prior to installing the transverse screws 105, alignment of the transverse screws 105 at the external surfaces of the bones with the transverse through holes 103 hidden inside of the bones may be challenging. To assist in alignment of the screws 105 with the holes 103, a guide 401 may be provided which identifies positions of the transverse through holes 103 with respect to the two or more bones. "Position" as used here may include longitudinal location along longitudinal axis 107 as well as rotational orientation about longitudinal axis 107. In an exemplary embodiment, a guide 401 such as is shown in FIGS. 4A and 4B includes a plate 403 with one or more guide holes 405 the centers of which are spaced apart identically to the spacing of the transverse through-holes 103 in the lag screw 101. An arm 407 is extendable from the plate 403 to the head 104 of the lag screw 101. In one embodiment, the arm 407 has a hexagonal cross section which fits into a hexagonal inset in the head 104. The head 104 and the transverse through holes 103 of the lag screw 101 have a fixed relationship to one another, typically because the lag screw 101 may be formed as one integral piece. More specifically, each transverse through hole 103 has a fixed longitudinal distance from head 104 and a fixed rotational orientation such that rotation of the head 104 an arbitrary number of degrees about the longitudinal axis 107 likewise gives a rotation of the transverse through holes 103 about the longitudinal axis 107 by exactly the same number of degrees. As a result, the position (e.g. both longitudinal location and rotational orientation) of the head 104 in three dimensional space and with respect to the bones may be used to ascertain the position of the transverse through holes 103 in three dimensional space and with respect to the bones. The guide 401 is configured to use this relationship between the head 104 and the transverse through holes 103. Once in place, the guide 401, using the position of the head 104, aligns the guide holes 405 with the transverse through holes 103 such that aligned pairs are substantially coaxial. Guide sleeves 410 may be inserted into the guide holes 405 to facilitate guiding drilling for and installation of transverse screws 105.

Figure 5A:
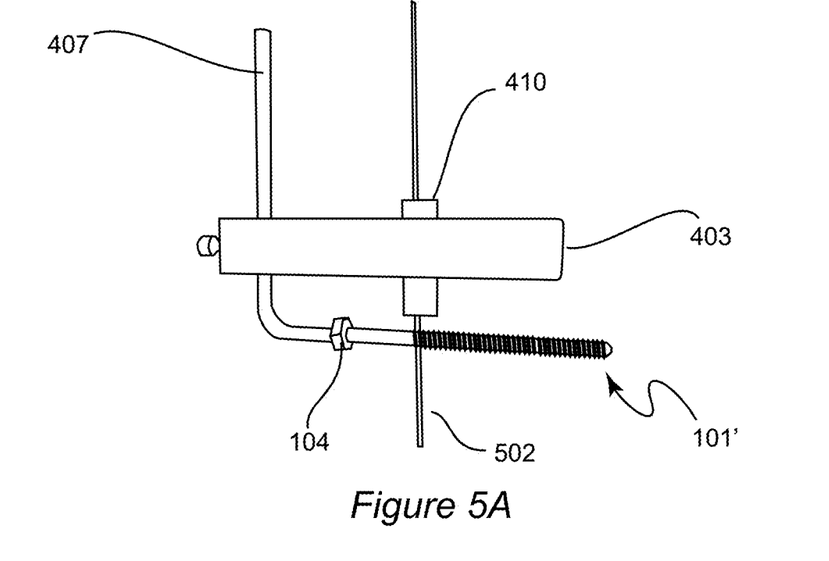
FIGS. 5A and 5B show a guide in use with an implant.
Figure 5B:
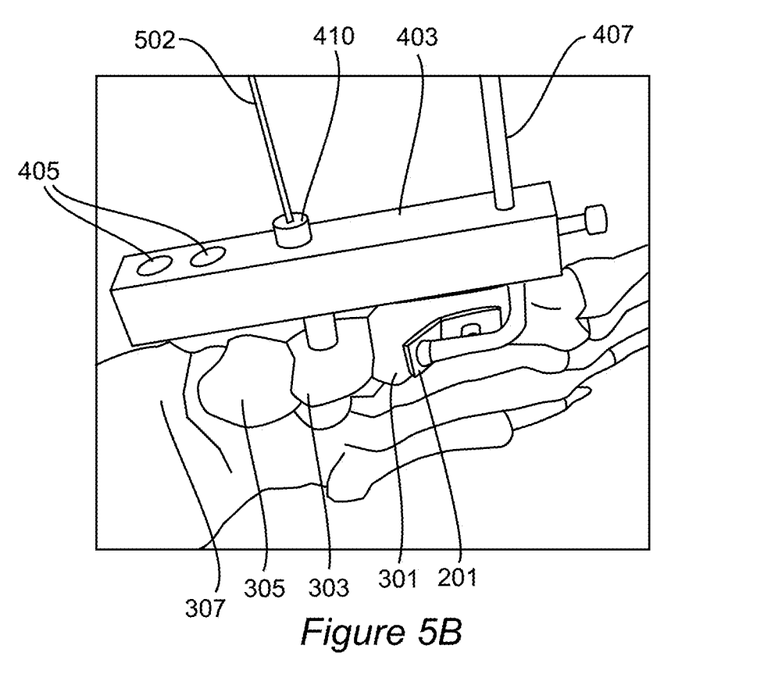

FIGS. 5A and 5B show a guide 401 in use with a lag screw 101' which is not presently inserted in a midfoot (FIG. 5A) and a lag screw which is inserted in a midfoot (FIG. 5B). As shown, a drill bit 502 is aligned by the guide 401 for drilling through bone tissue along a center axis of a transverse through hole 103 of the lag screw 101'. Note that lag screw 101' differs from a lag screw 101 as shown in FIGS. 1A-1C according the length of threaded portion 106b as compared to unthreaded portion 106a.

Figure 6:
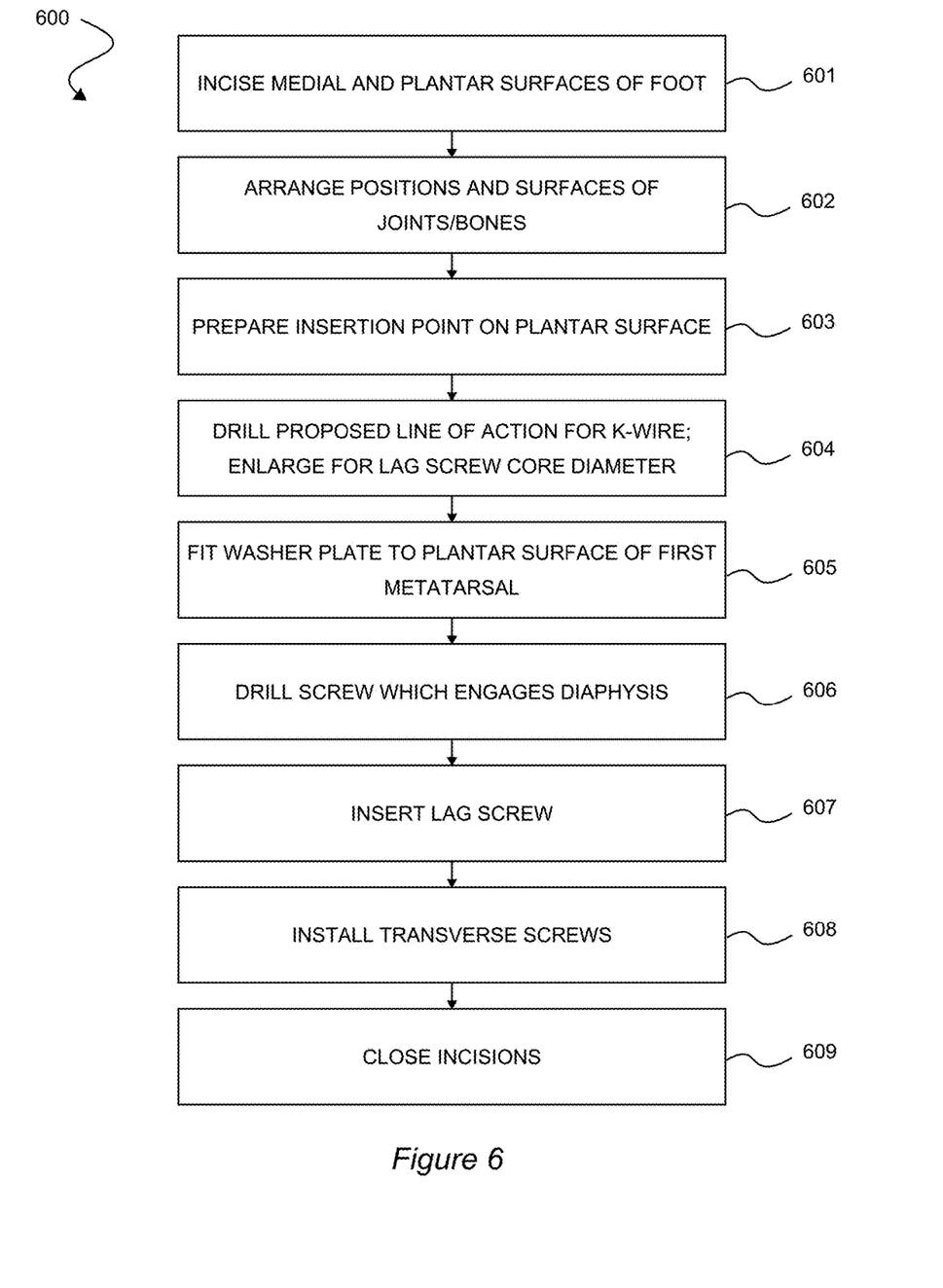
FIG. 6 shows a surgical method of midfoot arthrodesis.

FIG. 6 shows a method 600 of midfoot arthrodesis of one or more joints comprising two or more bones which include a first metatarsal in a foot. To install a lag screw 101 in a foot, incisions are generally first made on the foot in order to access the bones, e.g. the talus, navicular, medial cuneiform, first metatarsal, and the respective joints connecting these bones (step 601). These incisions will generally be made on the medial and plantar aspects of the foot and are used to arrange the bones (step 602). Arrangement of the bones includes arranging their positions relative to one another and removing soft tissue that would interfere with fusion. Once the bones are arranged, the insertion point for the lag screw may be prepared (step 603). To accomplish this, an incision may be made on the plantar surface of the foot slightly distal to the proximal head of the first metatarsal, and any material between the opening and the proximal head should be cleared out of the way. The plantar surface of the first metatarsal will serve as the insertion point of the lag screw 101.

At this point a hole may be drilled through the plantar surface of the first metatarsal penetrating each of the two or more bones (step 604). This may include first drilling a proposed line of action, originating at the plantar surface of the proximal head of the first metatarsal and crossing, for example, the transverse tarsal joint, the cuneonavicular joint, the tarsometatarsal joint, and ending in the talus. Then a k-wire may be installed, followed by a subsequent drilling or reaming to enlarge the hole to match the core diameter 108 of the lag screw 101. Once the hole has been cleared, a washer plate 201 may be fitted to the plantar surface of the first metatarsal (step 605). When this is done, some of the plantar surface of the first metatarsal near the proximal head may be shaped (e.g. bone tissue removed therefrom) in order to provide a flat surface for the washer plate 201 to be stable and evenly engaged with the metatarsal when compression has been induced. Once fitted, the superior hole of the washer plate 201 may have a standard screw drilled through it, engaging the diaphysis of the metatarsal due to the larger amount of cortical bone present (step 606). This bicortical screw helps ensure that the washer plate 201 does not loosen over time and may improve fusion and compression as the entire first metatarsal will be pulled during compression to fuse with the surface of the medial cuneiform.

Next, the lag screw 101 will be placed through the inferior hole of the washer plate 201 and inserted into the hole penetrating the bones, the insertion including rotation (e.g. clockwise) to engage the threading in the bone (step 607). Rotation is generally performed until two-finger tightness has been obtained from the compressive forces caused by the lag effect being transferred from the talus to the washer plate 201. When inserting the lag screw it is preferred that rotation be completed such that at its completion, the transverse through holes 103 line-up perpendicular to the median sagittal plane of the foot.

Next, transverse screws 105 will be installed in the transverse through holes 103 (step 608). This may be done using the incisions made earlier to arrange the bones for compression (steps 601/602). In some exemplary embodiments, a correctly placed guide 401 will lay parallel with the median sagittal plane of the foot, in line with the transverse through holes 103 of the inserted lag screw 101. The fixed positions of the transverse through-holes 103 with respect to the head 104 helps ensure that the transverse through holes 103 and the guide holes 405 of the guide 401 will be aligned even if the transverse through holes 103 are not directly perpendicular with the median sagittal plane. With the guide 401 in place, transverse screws 105 may be installed through any one or more of the transverse through holes 103 of the lag screw 101. X-ray in surgery may be used to verify the placement and penetration depth of the transverse screws 105 (e.g. to verify a bicortical nature, meaning that a transverse screw 105 goes through one bone cortex (i.e. the medial cortex of the bone) and then engages the cortex on the other side of the bone (i.e. lateral cortex, in a sagittal plane reference frame)). Generally, the heads of the transverse screws placed in the transverse through holes will sit on the surface of whatever bone they are installed in. It is desirable that the transverse screws penetrate into but not totally through the bone (e.g. the talus, navicular, or medial cuneiform). After the lag screw 101 and the transverse screws 105 are fully installed, the implant is complete and the incisions may be closed (step 609).

While exemplary embodiments of the present invention have been disclosed herein, one skilled in the art will recognize that various changes and modifications may be made without departing from the scope of the invention as defined by the following claims.

Having thus described our invention, what we claim as new and desire to secure by Letters Patent is:

1. An orthopedic implant for midfoot arthrodesis of one or more joints comprising two or more bones which include a first metatarsal in a foot, comprising:
    a lag screw having a head and a shaft with one or more transverse through holes, said shaft having a core diameter and a length which is long enough to permit penetration of said two or more bones via a drilled hole;
    one or more transverse screws installable in the one or more transverse through holes, each transverse screw having a length sufficient to be at least partially present in a transverse through hole of said lag screw and at least partially positionable in one of said two or more bones; and
    a washer plate configured to fit on a plantar surface of said first metatarsal.

2. The orthopedic implant of claim 1, wherein said washer plate includes a first hole with a diameter which is at least as large as said core diameter of said shaft and smaller than a diameter of said head such that insertion of said lag screw through said first hole and said drilled hole is such that said lag screw supplies compressive forces between said two or more bones and said washer plate.

3. The orthopedic implant of claim 2, wherein said washer plate further comprises a second hole configured to permit installation of a screw in a diaphysis of said first metatarsal without passing a head of said screw through said second hole when said washer plate is fitted on said plantar surface of said first metatarsal, wherein the second hole is superior to the first hole.

4. The orthopedic implant of claim 1, further comprising a k-wire insertable into said drilled hole, said lag screw being cannulated to permit guidance by said k-wire during insertion into said drilled hole.

5. The orthopedic implant of claim 1, wherein said one or more transverse through holes of said lag screw are perpendicular to said shaft.

6. The orthopedic implant of claim 1, wherein said one or more transverse through holes are a plurality of transverse through holes and said one or more transverse screws are a plurality of transverse screws.

7. The orthopedic implant of claim 6, wherein said plurality of transverse through holes are spaced apart from one another such that insertion of said lag screw into said drilled hole aligns at least one of said plurality of transverse screw holes with each of said two or more bones, permitting installation of at least one of said plurality of transverse screws in each of said two or more bones.

8. The orthopedic implant of claim 1, wherein said one or more joints include a transverse tarsal joint, a cuneonavicular joint, and a tarsometatarsal joint.

9. The orthopedic implant of claim 1, wherein the washer plate comprises a first hole and a second hole, wherein the second hole has a position displaced and at an angle with respect to the first hole such that, in a state of use by which the washer plate is fitted to a plantar surface of the first metatarsal, a center axis of the first hole is directable toward the medial cuneiform while the center axis of the second hole is directable toward the diaphysis of the first metatarsal.

10. An orthopedic surgical system for midfoot arthrodesis of one or more joints comprising two or more bones which include a first metatarsal in a foot, comprising:
    a lag screw having a head and a shaft with one or more transverse through holes, said shaft having a core diameter and a length which is long enough to permit penetration of said two or more bones via a drilled hole;
    one or more transverse screws installable in the one or more transverse through holes, each transverse screw having a length sufficient to be at least partially present in a transverse through hole of said lag screw and at least partially positionable in one of said two or more bones;
    a washer plate configured to fit on a plantar surface of said first metatarsal; and
    a guide which, when fitted to said head, identifies positions of said transverse through holes with respect to said two or more bones to permit alignment of said one or more transverse screws with said one or more transverse through holes.

11. The orthopedic surgical system of claim 10, wherein the washer plate comprises a first hole and a second hole, wherein the second hole has a position displaced and at an angle with respect to the first hole such that, in a state of use by which the washer plate is fitted to a plantar surface of the first metatarsal, a center axis of the first hole is directable toward the medial cuneiform while the center axis of the second hole is directable toward the diaphysis of the first metatarsal.

* * * * *